(12) United States Patent
Drent et al.

(10) Patent No.: US 7,135,542 B2
(45) Date of Patent: Nov. 14, 2006

(54) BIDENTATE LIGANDS FOR THE CARBONYLATION OF UNSATURATED COMPOUNDS

(75) Inventors: Eit Drent, Amsterdam (NL); Roelof Van Ginkel, Amsterdam (NL); Renata Helena Van Der Made, Amsterdam (NL)

(73) Assignee: Shell Oil Company, Houston, TX (US)

( * ) Notice: Subject to any disclaimer, the term of this patent is extended or adjusted under 35 U.S.C. 154(b) by 3 days.

(21) Appl. No.: 10/494,901

(22) PCT Filed: Nov. 5, 2002

(86) PCT No.: PCT/EP02/12380

§ 371 (c)(1),
(2), (4) Date: Aug. 3, 2004

(87) PCT Pub. No.: WO03/040159

PCT Pub. Date: May 15, 2003

(65) Prior Publication Data

US 2004/0259724 A1    Dec. 23, 2004

Related U.S. Application Data

(60) Provisional application No. 60/348,205, filed on Nov. 9, 2001.

(30) Foreign Application Priority Data

Jul. 18, 2002   (EP) .................................. 02077923

(51) Int. Cl.
    *C08G 69/08*    (2006.01)

(52) U.S. Cl. ...................... 528/310; 528/322; 528/392; 528/398

(58) Field of Classification Search ................. 528/310, 528/322, 392, 398; 502/167
See application file for complete search history.

(56) References Cited

U.S. PATENT DOCUMENTS

| 6,156,934 | A  | * | 12/2000 | Suykerbuyk et al. ......... 568/12 |
| 6,639,091 | B1 | * | 10/2003 | Drent et al. ................... 556/21 |
| 6,706,912 | B1 | * | 3/2004  | Drent et al. ................. 560/233 |
| 6,743,911 | B1 | * | 6/2004  | Drent et al. ................. 540/485 |
| 2004/0024258 | A1 | * | 2/2004 | Drent et al. ................. 568/429 |
| 2005/0059841 | A1 | * | 3/2005 | Drent et al. ................. 562/890 |
| 2005/0192457 | A1 | * | 9/2005 | Drent et al. ................. 560/232 |

FOREIGN PATENT DOCUMENTS

| WO | 98/42717 | 10/1998 |
| WO | 00/14055 | 3/2000 |
| WO | 01/72697 | 10/2001 |
| WO | 01/87899 | 11/2001 |

* cited by examiner

Primary Examiner—Duc Truong

(57) ABSTRACT

Bidentate ligand of formula (I), $R^1R^2M^1\text{-}R\text{-}M^2R^3R^4$ wherein $M^1$ and $M^2$ each indenpendently represent P, As or Sb; $R^1$, $R^2$, $R^3$ and $R^4$ each independently represent the same or a different optionally substituted organic group and at least one of $R^1$, $R^2$, $R^3$ and $R^4$ contains a tertiary carbon atom through which the group is linked to $M^1$ or $M^2$; and R represents a bridging group based on a trimethylene group connecting $M^1$ and $M^2$ of which the middle carbon atom is double bonded to a non-metal element chosen from group 14, 15 or 16 of the periodic table of elements. Catalyst comprising this bidentate ligand and carbonylation process n which this catalyst is used.

13 Claims, No Drawings

BIDENTATE LIGANDS FOR THE CARBONYLATION OF UNSATURATED COMPOUNDS

This application claims the benefit of U.S. Provisional Application 60/348,205, filed Nov. 9, 2001 and of PCT Application PCT/EP02/12380, filed Nov. 5, 2002, which designated the United States. This application claims foreign priority to European Application 02077923.7, filed Jul. 18, 2002.

This invention relates to a new class of bidentate ligands, a catalyst comprising such bidentate ligands and a process for the carbonylation of optionally substituted ethylenically or acetylenically unsaturated compounds by reaction with carbon monoxide and a coreactant in the presence of such a catalyst. This invention further specifically relates to the use of such a catalyst in a process for the carbonylation of a pentenenitrile or an alkylpentenoate.

WO-A-0172697 describes in its examples the carbonylation of a pentenenitrile by reaction thereof with carbon monoxide and methanol in the presence of a catalyst comprising palladium acetate, an acid and a bidentate diphosphine. The exemplified bidentate diphosphines are 1,3 bis(di-tert.-butylphosphino) propane and 1,2 bis(di-tert.-butylphosphino) ethane, and 1,2 bis(di-tert.-butylphosphino) benzene. Selectivities towards linear cyano-esters in the range of 88 to 98% are obtained. The highest initial rate of carbonylation obtained is 400 mol/mol/hr.

WO-A-0014055 describes in its examples the carbonylation of pentenenitrile by reaction thereof with carbon monoxide and methanol in the presence of catalyst comprising palladium acetate, anthracene carboxylic acid and a bidentate diphoshine. The exemplified bidentate diphoshines are 1,3-bis-(1,5-cyclooctylenephosphino) ethane, 1,2-bis-(1,4-cyclo-octylenephosphino)ethane and the mixed compound with 1,5- and 1,4-cyclooctylene groups (bcope); and 1,3-bis-(1,4-cyclooctylenephosphinomethyl)(2,4-difluorphenyl)amine, 1,3-bis-(1,5-cyclooctylenephosphinomethyl)(2,4-difluorphenyl)amine and 1-(1,4-cyclooctylenephosphinomethyl)-3-(1,5-cyclooctylenephosphinomethyl)(2,4-difluorphenyl)amine (azabcope). Selectivities towards linear cyano-esters in the range of 70 to 72% are obtained. The examples of WO-A-0014055 do not mention an initial rate of carbonylation.

The object of the present invention is to provide a catalyst in the presence of which a high reaction rate can be obtained in a process for the carbonylation of an optionally substituted ethylenically or acetylenically unsaturated compound, whilst still high selectivities towards a linear product can be obtained.

Such a catalyst has now been found. The catalyst having this advantageous effect comprises a new bidentate ligand.

Accordingly this invention provides a bidentate ligand of formula I, $$R^1R^2M^1\text{-}R\text{-}M^2R^3R^4 \quad (I)$$

wherein $M^1$ and $M^2$ each independently represent P, As or Sb;

$R^1$, $R^2$, $R^3$ and $R^4$ each independently represent the same or a different optionally substituted organic group and at least one of $R^1$, $R^2$, $R^3$ and $R^4$ contains a tertiary carbon atom through which the group is linked to $M^1$ or $M^2$; and R represents a bridging group based on a trimethylene group connecting $M^1$ and $M^2$ of which the middle carbon atom is double bonded to a non-metal element chosen from group 14, 15 or 16 of the periodic table of elements.

It is surprisingly found that the use of a catalyst comprising such a bidentate ligand in a process for the carbonylation of an optionally substituted ethylenically or acetylenically unsaturated compound results in exceptionally high reaction rates. Moreover, such high reaction rates can be obtained whilst maintaining high selectivities towards a linear carbonylation product. A further advantage can be found in the good stability of the catalyst during operation.

In the bidentate ligand of formula I, $M^1$ and $M^2$ are preferably the same and more preferably they both represent phosphorus atoms.

In the bidentate ligand of formula I, $M^1$ and $M^2$ are connected by a trimethylene group of which the middle carbon atom is double bonded to an element chosen from group 14, 15 or 16. A "trimethylene group" is understood in accordance with IUPAC nomenclature to be an optionally substituted bivalent radical derived from optionally substituted propane by removal of a hydrogen atom from each of the two terminal carbon atoms. The middle carbon atom of the trimethylene group is double bonded to a non-metal element chosen from group 14, 15 or 16 of the periodic table of elements. Preferably the middle carbon atom of the trimethylene group is double bonded to a silicon, nitrogen, oxygen or sulphur atom or to an additional carbon atom. Of those, carbon, oxygen and sulphur are especially preferred and carbon and oxygen are most preferred.

The non-metal element chosen from group 14, 15 or 16 can form part of an organic or inorganic group A, which is double bonded to the middle carbon atom of the trimethylene group via the non-metal element chosen from group 14, 15 or 16. Hence the trimethylene group can be a trimethylene group having the formula (II)

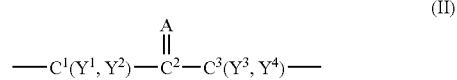

wherein $C^1$ and $C^3$ represent the outer carbon atoms of the trimethylene group, connected to respectively $M^1$ and $M^2$;

A represents an organic or inorganic group, which is double bonded to the middle carbon atom $C^2$ via a non-metal element chosen from group 14, 15 or 16 of the periodic table of elements; and $Y^1$, $Y^2$, $Y^3$ and $Y^4$ each independently represent a hydrogen atom or an organic group.

The group A preferably comprises in the range from 1 to 20 atoms, more preferably in the range from 1 to 10 atoms. It can comprise no carbon atoms or a carbon chain, which is optionally interrupted or substituted by heteroatoms such as N, O, S and P. If the group A comprises a carbon chain, the carbon chain can be saturated or non-saturated, linear or branched and it can contain cycloaliphatic or aromatic parts. Preferred groups A include groups of the structure =O, =S, =SiH_2, =SiHX, =SiX_2, =CH_2, =CHX, =CX_2, wherein X represents a hydrocarbyl group. The hydrocarbyl group X can contain hetero atoms such as N, O, S and P and can be saturated or non-saturated. It can be linear or branched or can contain cycloaliphatic or aromatic parts. Preferably X represents an alkyl group, preferably having from 1 to 20 carbon atoms, more preferably from 1 to 10 carbon atoms and most preferably from 1 to 6 carbon atoms. Examples of X include methyl, ethyl, propyl, iso-propyl, n-butyl, tert.-butyl, phenyl, cyclopentyl, cyclohexyl and tolyl. More preferably the group A represents a =O, =S, =CH$_2$, =CHX or =CX$_2$ group, and most preferably a =O (-oxo) or =CH$_2$ (-methylene) group.

Examples of possible trimethylene groups include: 2-oxo-trimethylene, 2-thioxo-trimethylene, 2-methylene-trimethylene and 2-ethylidene-trimethylene, 2-propylidene-trimethylene, 2-phenylidene-trimethylene, 2-diphenylmethylene-trimethylene. Of these 2-oxo-trimethylene and 2-methylene-trimethylene are preferred.

The trimethylene group connecting M$^1$ and M$^2$ can contain substituents on either one of the outer carbon atoms (C$^1$ and C$^3$), as for example illustrated by Y$^1$, Y$^2$, Y$^3$ and Y$^4$ in formulae II. Such substituent groups preferably comprise in the range of 1 to 20, more preferably 1 to 10 and most preferably 1 to 6 atoms. The substituents can contain carbon and/or heteroatoms, such as for example N, O, S or P. The substituents can be straight or branched and can comprise aromatic or cycloaliphatic parts. Examples of substituents include alkyl, cycloalkyl or aryl groups, such as a methyl, ethyl, propyl, iso-propyl, butyl, iso-butyl, tert.-butyl, pentyl, cyclohexyl, cyclopentyl, phenyl or tolyl.

Preferably the outer carbon atoms of the trimethylene group are non-substituted or only substituted with alkyl groups. That is, preferably Y$^1$, Y$^2$, Y$^3$ and Y$^4$ each independently represent hydrogen or an alkyl group, preferably having from 1 to 6 carbon atoms, such as methyl, ethyl, propyl and isopropyl, n-butyl, isobutyl or tert.-butyl. Most preferably Y$^1$, Y$^2$, Y$^3$ and Y$^4$ each independently represent hydrogen or a methyl group.

The trimethylene group forms part of the bridging group R. This bridging group can be linear or can comprise a cycloaliphatic or aromatic ring structure. For example Y$^1$, Y$^2$, Y$^3$ and Y$^4$ in formulae II can be connected to one another to form a cycloaliphatic ring structure. Preferably the bridging group comprises in the range from 3 to 20, more preferably from 3 to 10 carbon atoms. In addition to carbon atoms the bridging group can contain heteroatoms, such as nitrogen, sulphur, silicon or oxygen. Preferably the bridging group comprises a carbon-chain which is not interrupted by heteroatoms.

Examples of preferred bridging groups R thus include 2-oxo 1,3-trimethylene; 3-oxo 2,4-pentamethylene; 1,3-diphenyl, 2-oxo 1,3-trimethylene; 1,3-dipropyl, 2-oxo 1,3-trimethylene; 2-methylene 1,3-trimethylene; 3-methylene 2,4-pentamethylene; 1,3-diphenyl, 2-methylene 1,3-trimethylene; 1,3-dipropyl, 2-methylene 1,3-tri-methylene; 2-ethylidene 1,3-trimethylene; 3-ethylidene 2,4-pentamethylene; 1,3-diphenyl, 2-ethylidene 1,3-trimethylene; 1,3-dipropyl, 2-ethylidene 1,3-trimethylene; 2-thioxo 1,3-trimethylene; 3-thioxo 2,4-pentamethylene; 1,3-diphenyl, 2-thioxo 1,3-trimethylene; wherein the two free valencies are bonded to M$^1$ and M$^2$.

Of these the following bridging groups R are most preferred: 2-oxo 1,3-trimethylene; 3-oxo 2,4-pentamethylene; 2-methylene 1,3-trimethylene; 3-methylene 2,4-pentamethylene; wherein the two free valencies are bonded to M$^1$ and M$^2$.

R$^1$, R$^2$, R$^3$ and R$^4$ each independently represent the same or a different optionally substituted organic group and at least one of R$^1$, R$^2$, R$^3$ and R$^4$ contains a tertiary carbon atom through which the group is linked to M$^1$ or M$^2$. The organic groups preferably have from 4 to 20 carbon atoms and more preferably from 4 to 8 carbon atoms. The organic groups not comprising a tertiary carbon atom through which the group is linked to M$^1$ or M$^2$, are preferably linked to M$^1$ or M$^2$ via a secondary carbon atom. More preferably, however, two or more of R$^1$, R$^2$, R$^3$ and R$^4$ contain a tertiary carbon atom through which the group is linked to M$^1$ or M$^2$.

Most preferably, each of R$^1$, R$^2$, R$^3$ and R$^4$ contains a tertiary carbon atom through which the group is linked to M$^1$ or M$^2$.

The tertiary carbon atom can be substituted with aliphatic, cyclo-aliphatic or aromatic substituents or can form part of a substituted saturated or non-saturated aliphatic ring structure. Hence examples of possible organic groups include tert.-butyl, 1,1-dimethyl-propyl, 1-methyl-1-ethyl-propyl, 1-methyl-1-phenyl-propyl, 1,1-diethylpropyl, 1,1-diphenyl-propyl, 1,1,1-triphenylmethyl, 1,1-dimethyl-butyl, 1-methyl-1-ethyl-butyl, 1,1-diethylbutyl, 1,1-diphenylbutyl, 1,1,3,3-tetramethylbutyl and 1-(1-methyl)cyclohexyl groups. Preferably the tertiary carbon atom is substituted with alkyl groups, i.e. preferably the organic group is a tertiary alkyl group. Of these, tert.-butyl groups are most preferred. Preferably the groups R$^1$, R$^2$, R$^3$ and R$^4$ represent the same tertiary alkyl groups, most preferably groups R$^1$, R$^2$, R$^3$ and R$^4$ are tert.-butyl groups.

Examples of possible ligands include
1,3-bis(di-tert.-butylphosphino)2-methylene-propane (in IUPAC nomenclature this compound is referred to as 3-(di-tert.-butylphosphino)-2-(di-tert.-butylphosphinomethyl)-1-propene); 1,3-bis(di-tert.-butylphosphino)2-propanone; 1,3-bis(di-tert.-butylphosphino)2-propathione;
2,4-bis(di-tert.-butylphosphino)3-pentanone; 2,4-bis(di-tert.-butylphosphino)3-pentathione; 2,4-bis(di-tert.-butylphosphino)3-methylene-pentane (in IUPAC nomenclature this compound is referred to as 3-(di-tert.-butylphosphino)-2-(1-[di-tert.-butylphosphino]-ethyl)-1-butene);
2,5-bis(di-tert.-butylphosphino)1-cyclopentanone;
2,6-bis(di-tert.-butylphosphino)1-cyclohexanone;
2,5-bis(di-tert.-butylphosphino)1-cyclopentathione;
2,6-bis(di-tert.-butylphosphino)1-cyclohexathione;
1,3-bis[di-2-(2-methyl)butylphosphino]2-butanone;
1,3-bis[di-2-(2-ethyl)butylphosphino]2-butathione.

Especially preferred bidentate ligands are 1,3-bis(di-tert.-butylphosphino)2-methylene-propane (in IUPAC nomenclature this compound is referred to as 3-(di-tert.-butylphosphino)-2-(di-tert.-butylphosphinomethyl)-1-propene); 1,3-bis(di-tert.-butylphosphino)2-propanone.

The above ligands with a bridging group R can be prepared in a manner analogous to the preparation of 3-(di-tert.-butylphosphino)-2-(di-tert.-butylphosphinomethyl)-1-propene, which is exemplified in example 1. For example, 1,3-bis(di-tert.-butyl-phosphino)2-propanone can be prepared by reacting di-tert.-butylphosphine with 1,3-dichloro-2-propanone.

Without wishing to be bound to any theory it is thought that during a carbonylation reaction of an optionally substituted ethylenically or acetylenically unsaturated compound by reaction thereof with carbon monoxide and a coreactant in the presence of a catalyst comprising the bidentate ligand of formula I, the bidentate ligand of formula I can be in-situ converted into a derivative thereof. For example, if the co-reactant is a hydroxy-group containing compound, the bidentate ligand can be converted into the reaction product of the bidentate ligand of formula I and this hydroxy-group containing compound.

Especially the double bond between the middle carbon atom of the trimethylene group and the non-metal element from group 14, 15 or 16 is thought to be susceptible to reaction with the co-reactant during a carbonylation reaction.

If the double bond of the bidentate ligand of formula I reacts with a hydroxy-group containing compound, the resulting bidentate ligand can comprise a bridging group wherein the double bond is replaced by for example an ester, an alkoxy or an hydroxy group.

The invention further provides a catalyst comprising:
(a) a source of group VIII metal cations;
(b) a bidentate ligand of formula (I) as described above; and
(c) a source of anions.

In the present specification the group VIII metals are defined as the metals rhodium, nickel, palladium and platinum. Of these, palladium and platinum are preferred.

Examples of suitable metal sources are platinum or palladium compounds such as salts of palladium or platinum and nitric acid, sulphuric acid or acids, salts of platinum or palladium and carboxylic acids with up to 12 carbon atoms, palladium- or platinum complexes, e.g. with carbon monoxide or acetylacetonate, or palladium or platinum combined with a solid material such as an ion exchanger. Palladium(II) acetate and platinum(II) acetylacetonate are examples of preferred metal sources.

The molar ratio between the bidentate ligand (b) and the group VIII metal (a) is preferably in the range of 1:1 to 5:1 and, more preferably, in the range of 1:1 to 3:1. The possibility of applying these low molar ratios is advantageous, as it avoids the use of an excess of bidentate ligand and hence minimises the consumption of these usually expensive compounds.

As anion source, any compound generating these anions may be used. Suitably, acids, or salts thereof, are used as source of anions, for example any of the acids mentioned above, which may also participate in the salts of the group VIII metal.

In the catalyst systems of the invention, preferably acids are used as anion source, preferably acids having a pKa value of less than 6, more preferably less than 5, and most preferably less than 3, measured in aqueous solution at 18° C.

Examples of suitable anions include anions of carboxylic acids; phosphoric acid; phosphonic acids, such as methyl phosphonic acid or phenyl phosphonic acid; sulphuric acid; sulphonic acids; and halogenated carboxylic acids such as trifluoroacetic acid.

Carboxylic acids that can be used include saturated or non-saturated, straight, branched or cyclic carboxylic acids with preferably up to 12 carbon atoms, and more preferably up to 6 carbon atoms, such as for example, pentanoic acid, pivalic acid, propionic acid and propenoic acid.

Sulphonic acids are in particular preferred, for example methanesulphonic acid, trifluoromethanesulphonic acid, tert.-butane-sulphonic acid, p-toluenesulphonic acid and 2,4,6-trimethylbenzene-sulphonic acid. Ion exchangers containing sulphonic acid groups, such as, for example, AMBERLITE 252H ("AMBERLITE" is a trade name) can also be used.

Also, complex anions are suitable, such as the anions generated by a combination of a Lewis acid such as $BF_3$, $AlCl_3$, $SnF_2$, $Sn(CF_3SO_3)_2$, $SnCl_2$ or $GeCl_2$, $AsF_5$, $SbF_5$, $PF_5$, $TaF_5$ or $NbF_5$, with a protic acid, such as a sulphonic acid, e.g. $CF_3SO_3H$ or $CH_3SO_3H$ or a hydrohalogenic acid such as HF of HCl, or a combination of a Lewis acid with an alcohol. Examples of such complex anions include $BF_4-$, $SnCl_3-$, $[SnCl_2.CF_3SO_3]-$ and $PF_6-$.

The molar ratio of acid and mole atom of Group VIII metal (a) is preferably between 1:1 and 10:1 and more preferably between 1:1 and 5:1.

Use of the catalyst in a process for the carbonylation of an optionally substituted ethylenically or acetylenically unsaturated compound results in advantageous high reaction rates.

Accordingly the present invention also provides a process for the carbonylation of an optionally substituted ethylenically or acetylenically unsaturated compound by reaction thereof with carbon monoxide and a coreactant in the presence of a catalyst as described herein.

As indicated above during this process, the bidentate ligand of formula I can in-situ be converted into a derivative thereof. Hence, this invention also provides a process for the carbonylation of an optionally substituted ethylenically or acetylenically unsaturated compound by reaction thereof with carbon monoxide and a coreactant in the presence of a catalyst as described above wherein the bidentate ligand of formula (I) has been replaced by an in-situ formed derivative thereof.

The ethylenically or acetylenically unsaturated compound, used as starting material, is preferably an ethylenically or acetylenically unsaturated compound having from 2 to 20 carbon atoms per molecule, or a mixture thereof. They may comprise one or more unsaturated bonds per molecule. Preferred are compounds having from 2 to 10 carbon atoms and more preferred compounds having from 2 to 6 carbon atoms, or mixtures thereof. The ethylenically unsaturated compound can be cyclic or branched and can contain aromatic or cycloaliphatic parts. The ethylenically or acetylenically unsaturated compound can further comprise functional groups or heteroatoms, such as nitrogen, sulphur, phosphorus or oxide. Examples include unsaturated carboxylic acids, esters of such acids or alkene nitriles. Examples of unsaturated compounds include ethene, propene, 2-butene, 1-, or 2-pentene, 1-, 2- or 3-hexene, cyclohexene, cyclopentene, ethyne, propyne, butyne, pentyne, 2-, 3- or 4-pentenenitrile, methylpentenoate, ethylpentenoate, propylpentenoate, 1,3-butadiene, 1,4-hexadiene and 1,3,5-hexatriene.

The process of the invention has been found especially advantageous in the carbonylation of pentenenitriles (e.g. 2-, 3- or 4-pentenenitrile) and alkyl pentenoates. Preferred alkylpentenoates are those with an alkyl group having in the range from 1 to 6 carbon atoms, for example methyl pentenoate and ethylpentenoate. Methylpentenoate is especially preferred.

Preferred co-reactants include molecular hydrogen and hydroxyl-group containing compounds. Hydroxyl-group containing compounds are especially preferred. Preferred hydroxyl-group containing compounds include water and alkanols. Preferred alkanols are mono-alkanols and di-alkanols having in the range from 1 to 10, more preferably in the range from 1 to 6 carbon atoms.

Especially preferred co-reactants include methanol, ethanol, isopropanol, n-propanol, n-butanol, iso-butanol, pentanol, hexanol, phenol, ethylene glycol and 1,3-propane diol. Of these, methanol and ethanol are most preferred.

The amount of co-reactant is not critical. The molar ratio of co-reactant to unsaturated compound can range from about equimolar to an excess of co-reactant.

Preferably the molar ratio of co-reactant to unsaturated compound ranges from 1:1 to 104:1, more preferably to 100:1 and most preferably to 10:1.

Carbon monoxide partial pressures in the range of 1–65 bar are preferred. In the process according to the present invention, the carbon monoxide can be used in its pure form or diluted with an inert gas such as nitrogen, carbon dioxide or noble gases such as argon.

In the process of the invention, the unsaturated starting material, the formed product and optionally the co-reactant can act as reaction diluent. Hence, the use of a separate solvent is not necessary. Conveniently, however, the carbonylation reaction may be carried out in the additional presence of a solvent. Examples of such solvents include saturated hydrocarbons such as paraffins and isoalkanes; ethers such as 2,5,8-trioxanonane (diglyme), di-butyl-ether and anisole, and ketones, such as methylbutylketone. Solvents, comprising or substantially consisting of sulphones are also preferred. Sulphones are in particular preferred, for example dialkylsulphones such as dimethylsulphone and diethyl-sulphone and cyclic sulphones, such as sulfolane (tetrahydrothiophene-2,2-dioxide), 2-methylsulfolane and 2-methyl-4-ethylsulfolane.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of Group. VIII metal per mole of ethylenically unsaturated compound are used.

The carbonylation of pentene-nitrile is an important step in a possible synthesis route for the preparation of ε-caprolactam, an intermediate in the preparation of Nylon 6. The present invention therefore also provides a process for the preparation of ε-caprolactam comprising
(i) carbonylation of a pentenenitrile to 5-cyanovaleric acid or an ester derivative thereof according to a process as described herein;
(ii) reduction of 5-cyanovaleric acid or ester derivative thereof as obtained in step (i) to 6-aminocaproic acid or ester;
(iii) cyclisation of the 6-aminocaproic acid or ester to ε-caprolactam.

The carbonylation of pentene-nitrile is further an important step in a possible synthesis route for the preparation of adipic acid or an ester or diester derivative thereof. Adipic acid and its ester derivatives are possible intermediates in the preparation of Nylon 6,6.

The present invention therefore also provides a process for the preparation of adipic acid or a ester or di-ester derivative thereof by
(I) carbonylation of pentenenitrile to 5-cyanovaleric acid or an ester derivative thereof according to the process as described herein;
(II) hydrolyse/esterification of 5-cyanovaleric acid or ester as obtained in step (I) to adipic acid or an ester or di-ester derivative thereof.

In a preferred embodiment the pentenenitrile of step i) or I) is obtained by hydrocyanation of butadiene with hydrogen cyanide as described in for example U.S. Pat. No. 4,298,546 and U.S. Pat. No. 5,821,378.

The other intermediate to prepare Nylon 6,6, 1,6-hexanediamine, can conveniently be prepared from pentenenitrile or butadiene by
hydrocyanation of pentenenitrile or butadiene to prepare 1,4-dicyano-butane;
hydrogenation 1,4-dicyano-butane to 1,6-hexanediamine.

Conveniently a process for the preparation of Nylon 6,6 therefore comprises:
(A) Preparation of adipic acid or a mono-ester or diester derivative thereof according to a process as described above;
(B) Preparation of 1,6-hexanediamine by hydrocyanation of pentenenitrile or butadiene to prepare 1,4-dicyano-butane and subsequent hydrogenation 1,4-dicyano-butane to 1,6-hexanediamine;
(C) Preparation of Nylon 6,6 by polymerisation of the adipic acid or a mono-ester or diester derivative thereof of step (A) with the 1,6-hexanediamine of step (B).

The invention will be illustrated by the following non-limiting examples.

EXAMPLE 1

Preparation of 3-(di-tert.-butylphosphino)-2-(di-tert.-butylphosphinomethyl)-1-propene A 50 ml Schlenk vessel under argon atmosphere is charged with 10 g (68 mmol) of di-tert.-butylphosphine, 4 g (32 mmol) of 3-chloro-2-chloromethyl-1-propene and 25 ml of acetonitrile. The mixture is refluxed for 40 hours. A precipitate of bisphosphonium salt is formed. After cooling to room temperature the bisphosphonium salt is isolated by filtration and drying.

To a stirred suspension of the bisphosphonium salt in 20 ml of toluene a 20% solution of NaOH is slowly added, until all of the bisphosphonium salt has been liberated and the water layer remains basic. The water layer is removed and the toluene layer extracted two more times with 10 ml of water. The toluene is removed by evaporation under reduced pressure, leaving a white solid, which is recrystallized from 30 ml of methanol at −35° C. Filtering and drying yields 7.3 g (21 mmol, 66%) of 3-(di-tert.-butylphosphino)-2-(di-tert.-butylphosphinomethyl)-1-propene as white crystals. The crystals were characterized as follows:
$^{31}P$ NMR ($C_6D_6$): 20.4
$^1H$ NMR ($C_6D_6$): 5.06 (2H, d, $CH_2$=), 2.63 (4H, dd, $CH_2P$), 1.13 (36H, d, tBu)

EXAMPLES 2–6 AND COMPARATIVE EXAMPLES A AND B

Carbonylation of Pentenenitrile and methyl-pentenoate

The experiments were carried out in a 250 ml Hastelloy C autoclave. The autoclave was charged with 0.25 mmol of palladium(II) acetate, 0.4 mmol of the bidentate diphosphine ligand as indicated in Table I, 1 mmol of methane sulphonic acid, 20 ml of the substrate as indicated in Table I, 10 ml of methanol and 40 ml of the solvent anisole. After being flushed with nitrogen, the autoclave was pressurized with carbon monoxide to a partial pressure of 30 bar. Subsequently, the reactor was sealed and the contents were heated to the temperature of 100° C. for 5 hours. The initial rate of carbonylation is indicated in Table I. The initial rate of carbonylation is defined as the mean rate of carbon monoxide consumption over the first 30% substrate conversion. After cooling, a sample was taken from the contents of the reactor and analyzed by GLC. The selectivity towards the desired linear product, i.e. the 5-cyano valeric methyl ester, based on the total amount of product formed is indicated in Table I.

EXAMPLE 7

Semi-Continuous Operation

Example 7 was carried out as described for example 4 during 5 hours. Hereafter an addition amount of 20 mol was added to the autoclave and the autoclave was pressurized with 30 bar carbon monoxide again. The reaction proceeded at 100° C. for an additional 5 hours. 97% of the pentenenitrile was converted to methyl cyano valeric esters. The selectivity towards the linear 5-cyano valeric methyl ester was 95% based on the total amount of product formed.

EXAMPLE 8

Carbonylation of Ethene

Example 8 was carried out as described for example 3, except that the autoclave was charged with 0.05 mmol palladium(II) acetate, 0.06 mmol of 1,3-bis(di-tert.-butylphosphino)2-propanone, 0.2 mmol of methane sulphonic acid and 50 ml of methanol.

The autoclave was pressurized with carbon monoxide to a partial pressure of 30 bar and ethene to a partial pressure of 20 bar. After 5 minutes conversion was 100%. The initial rate of carbonylation was 50.000 mol/mol/hr. The selectivity towards methyl-propionate was found to be 99.2% on total amount of product formed.

TABLE I

| Example | Bidentate ligand | Substrate | Initial rate of carbonylation (mol/mol/hr) | Time in which 80% conversion is reached (hours) | Selectivity to linear cyanovaleric ester (%) |
|---|---|---|---|---|---|
| 2 | dtbpm | methyl-3-pentenoate | 830 | 3 | 92 |
| 3 | dtbpo | methyl-3-pentenoate | 1700 | 1.5 | 95 |
| A | dtbpp | methyl-3-pentenoate | 450 | 7 | 95 |
| 4 | dtbpm | 3-pentenenitrile | 1850 | 2 | 93 |
| 5 | dtbpo | 3-pentenenitrile | 1000 | 3.5 | 96 |
| B | dtbpp | 3-pentenenitrile | 200 | 10 | 96 |
| 6 | dtbpm | 2-butene | 2000 | 1.1 | 93 | dtbpm = 1,3-bis(di-tertiarybutylphosphino)2-methylene-propane
dtbpo = 1,3-bis(di-tertiarybutylphosphino)2-propanone
dtbpp = 1,3-bis(di-tertiarybutylphosphino)propane

We claim:

1. A bidentate ligand of formula I, $$R^1R^2M^1\text{-}R\text{-}M^2R^3R^4 \qquad (I)$$

wherein $M^1$ and $M^2$ each independently represent P, As or Sb;

$R^1$, $R^2$, $R^3$ and $R^4$ each independently represent the same or a different optionally substituted organic group and at least one of $R^1$, $R^2$, $R^3$ and $R^4$ contains a tertiary carbon atom through which the group is linked to $M^1$ or $M^2$; and, R represents a bridging group based on a trimethylene group connecting $M^1$ and $M^2$ of which the middle carbon atom is double bonded to a non-metal element selected from the group consisting of elements of groups 14, 15 and 16 of the periodic table of elements.

2. The bidentate ligand according to claim 1 wherein the trimethylene group is a trimethylene group having the formula (II)

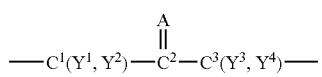

(II)

wherein $C^1$ and $C^3$ represent the outer carbon atoms of the trimethylene group, connected to respectively $M^1$ and $M^2$;

A represents an organic group, which is double bonded to the middle carbon atom $C^2$ via said non-metal element; and $Y^1$, $Y^2$, $Y^3$ and $Y^4$ each independently represents a hydrogen atom or an organic group.

3. The bidentate ligand according to claim 1 wherein said non-metal element is selected from the group consisting of carbon, oxygen and sulphur.

4. The bidentate ligand according to claim 1 wherein each of $R^1$, $R^2$, $R^3$ and $R^4$ contains a tertiary carbon atom through which the group is linked to $M^1$ or $M^2$.

5. A catalyst comprising:
(a) a source of group VIII metal cations;
(b) a bidentate ligand of formula (I)

$$R^1R^2M^1\text{-}R\text{-}M^2R^3R^4 \qquad (I)$$

wherein $M^1$ and $M^2$ each independently represent P, As or Sb;

$R^1$, $R^2$, $R^3$ and $R^4$ each independently represent the same or a different optionally substituted organic group and at least one of $R^1$, $R^2$, $R^3$ and $R^4$ contains a tertiary carbon atom through which the group is linked to $M^1$ or $M^2$; and, R represents a bridging group based on a trimethylene group connecting $M^1$ and $M^2$ of which the middle carbon atom is double bonded to a non-metal element selected from the group consisting of elements of groups 14,15 and 16 of the periodic table of elements; and, (c) a source of anions.

6. A process for the carbonylation of an optionally substituted ethylenically or acetylenically unsaturated compound by reaction thereof with carbon monoxide and a coreactant in the presence of the catalyst of claim 5.

7. A process for the preparation of ε-caprolactam comprising:
(i) carbonylation of pentenenitrile to 5-cyanovaleric acid or an ester derivative thereof according to the process of claim 6;
(ii) reduction of 5-cyanovaleric acid or ester derivative thereof as obtained in step (i) to 6-aminocaproic acid or ester; and,
(iii) cyclisation of the 6-aminocaproic acid or ester to ε-caprolactam.

8. A process for the preparation of Nylon 6, comprising preparing ε-caprolactam according to the process of claim 7 and then polymerising the ε-caprolactam.

9. A process for the preparation of adipic acid or a ester or di-ester derivative thereof by (I) carbonylation of pentenenitrile to 5-cyanovaleric acid or an ester derivative thereof according to the process of claim 6; and,
(II) hydrolyse/esterification of 5-cyanovaleric acid or ester as obtained in step (I) to adipic acid or an ester or di-ester derivative thereof.

10. A process for the preparation of Nylon 6,6 comprising:
(A) Preparation of adipic acid or a mono-ester or diester derivative thereof according to the process of claim 9;
(B) Preparation of 1,6-hexanediamine by hydrocyanation of pentenenitrile or butadiene to prepare 1,4-dicyano-butane and subsequent hydrogenation 1,4-dicyano-butane to 1,6-hexanediamine; and,
(C) Preparation of Nylon 6,6 by polymerisation of the adipic acid or a mono-ester or diester derivative thereof of step (A) with the 1,6-hexanediamine of step (B).

11. The bidentate ligand according to claim 2 wherein said non-metal element is selected from the group consisting of carbon, oxygen and sulphur.

12. The bidentate ligand according to claim 2 wherein each of $R^1$, $R^2$, $R^3$ and $R^4$ contains a tertiary carbon atom through which the group is linked to $M^1$ or $M^2$.

13. The bidentate ligand according to claim 3 wherein each of $R^1$, $R^2$, $R^3$ and $R^4$ contains a tertiary carbon atom through which the group is linked to $M^1$ or $M^2$.

* * * * *